United States Patent
Navve et al.

(10) Patent No.: US 9,259,231 B2
(45) Date of Patent: Feb. 16, 2016

(54) COMPUTER AIDED IMAGE-BASED ENHANCED INTRACORPOREAL LITHOTRIPSY

(71) Applicant: Gyrus ACMI, Inc., Southborough, MA (US)

(72) Inventors: Adi Navve, Kfar-Saba (IL); Shai Finkman, Haifa (IL)

(73) Assignee: Gyrus ACMI, Inc., Southborough, MA (US)

( * ) Notice: Subject to any disclaimer, the term of this patent is extended or adjusted under 35 U.S.C. 154(b) by 5 days.

(21) Appl. No.: 14/274,726

(22) Filed: May 11, 2014

(65) Prior Publication Data

US 2015/0320433 A1    Nov. 12, 2015

(51) Int. Cl.
| | |
|---|---|
| *A61B 8/00* | (2006.01) |
| *A61B 17/225* | (2006.01) |
| *A61B 18/26* | (2006.01) |
| *A61B 18/00* | (2006.01) |

(52) U.S. Cl.
CPC ............ *A61B 17/2256* (2013.01); *A61B 18/26* (2013.01); *A61B 2018/00511* (2013.01); *A61B 2018/00642* (2013.01); *A61B 2018/00702* (2013.01); *A61B 2018/00982* (2013.01)

(58) Field of Classification Search
CPC ...... A61B 8/0858; A61B 8/4455; A61B 8/13; A61B 8/4438; A61B 19/50; A61B 2017/00769; A61B 2019/5276
See application file for complete search history.

(56) References Cited

U.S. PATENT DOCUMENTS

| | | |
|---|---|---|
| 4,316,467 A | 2/1982 | Muckerheide |
| 4,669,483 A | 6/1987 | Hepp et al. |
| 4,682,594 A | 7/1987 | Mok |
| 4,763,652 A | 8/1988 | Brisson et al. |
| 4,887,605 A | 12/1989 | Angelsen et al. |
| 4,939,336 A | 7/1990 | Meyer et al. |
| 4,942,878 A | 7/1990 | Dory |

(Continued)

FOREIGN PATENT DOCUMENTS

| | | |
|---|---|---|
| CA | 2362332 A1 | 8/2000 |
| CN | 1515231 A | 7/2004 |

(Continued)

OTHER PUBLICATIONS

ELMED Lithotripsy Systems, VIBROLITH PLUS, Intracorporeal Ultrasonic Plus Pneumatic Lithotripter with Integrated Adjustable Suction Device, 4 pages, Dec. 3, 2008.

(Continued)

*Primary Examiner* — Joel Lamprecht
(74) *Attorney, Agent, or Firm* — D. Kligler IP Services Ltd.

(57) ABSTRACT

An apparatus is configured to deliver destructive energy to a stone. The apparatus includes a detector operative to obtain image data from the stone, a generator operating according to one or more producing parameters for producing the destructive energy, and a video processor unit receiving the image data from the detector. The video processor unit is operative to analyze the image data to determine a displacement of the stone relative to a previous location of the stone. A controller linked to the video processor unit and to the generator is operative to vary the one or more producing parameters of the generator responsively to the displacement of the stone. Methods carried out by the apparatus are further provided.

5 Claims, 6 Drawing Sheets

(56) References Cited

U.S. PATENT DOCUMENTS

| | | |
|---|---|---|
| 4,984,575 A | 1/1991 | Uchiyama et al. |
| 5,358,466 A | 10/1994 | Aida et al. |
| 5,473,136 A | 12/1995 | Engelhardt et al. |
| 5,531,739 A | 7/1996 | Trelles |
| 5,643,250 A | 7/1997 | O'Donnell |
| 5,697,885 A | 12/1997 | Konomura et al. |
| 5,749,830 A | 5/1998 | Kaneko et al. |
| 6,375,651 B2 | 4/2002 | Grasso et al. |
| 6,454,761 B1 | 9/2002 | Freedman |
| 7,967,016 B2 | 6/2011 | Anderson et al. |
| 8,006,702 B2 | 8/2011 | Lin |
| 8,235,968 B2 | 8/2012 | Tremaglio |
| 8,414,472 B2 | 4/2013 | Hagelauer |
| 8,535,250 B2 | 9/2013 | Owen et al. |
| 8,535,293 B2 | 9/2013 | Faherty et al. |
| 8,607,634 B2 | 12/2013 | Bailey et al. |
| 8,659,646 B2 | 2/2014 | Adler et al. |
| 8,753,332 B2 | 6/2014 | Bragagna et al. |
| 2002/0103477 A1 | 8/2002 | Grasso, III et al. |
| 2002/0119116 A1 | 8/2002 | Sahatjian et al. |
| 2003/0149352 A1 | 8/2003 | Liang et al. |
| 2004/0242961 A1 | 12/2004 | Bughici et al. |
| 2004/0243123 A1 | 12/2004 | Grasso, III et al. |
| 2005/0131339 A1 | 6/2005 | Makin et al. |
| 2006/0020269 A1 | 1/2006 | Cheng |
| 2006/0184076 A1 | 8/2006 | Gill et al. |
| 2007/0016113 A1 | 1/2007 | Buchholtz et al. |
| 2007/0016114 A1 | 1/2007 | Buchholtz et al. |
| 2007/0021754 A1 | 1/2007 | Chernenko et al. |
| 2007/0260112 A1 | 11/2007 | Rahmani |
| 2008/0226029 A1 | 9/2008 | Weir et al. |
| 2009/0275832 A1 | 11/2009 | Gelbart et al. |
| 2009/0275866 A1 | 11/2009 | Gilbart et al. |
| 2010/0092054 A1 | 4/2010 | Hensley et al. |
| 2010/0185187 A1 | 7/2010 | Yamashita et al. |
| 2011/0034832 A1 | 2/2011 | Cioanta et al. |
| 2011/0054363 A1 | 3/2011 | Cain et al. |
| 2011/0074943 A1 | 3/2011 | Modell et al. |
| 2011/0082452 A1 | 4/2011 | Melsky et al. |
| 2011/0257523 A1 | 10/2011 | Hastings et al. |
| 2011/0257561 A1* | 10/2011 | Gertner .............. A61B 5/412 600/411 |
| 2011/0263967 A1 | 10/2011 | Bailey et al. |
| 2012/0316396 A1 | 12/2012 | Robertson |
| 2013/0072753 A1 | 3/2013 | Zappia et al. |
| 2013/0102932 A1* | 4/2013 | Cain ................. A61N 7/00 601/2 |
| 2013/0116561 A1* | 5/2013 | Rothberg ............ A61B 8/4254 600/438 |
| 2013/0211294 A1 | 8/2013 | Bohris |
| 2014/0276101 A1 | 9/2014 | Asselin et al. |
| 2014/0336497 A1* | 11/2014 | Gertner .............. A61B 5/055 600/411 |
| 2015/0055821 A1 | 2/2015 | Fotland |
| 2015/0078615 A1 | 3/2015 | Staples, II et al. |
| 2015/0213616 A1 | 7/2015 | Kappeler et al. |

FOREIGN PATENT DOCUMENTS

| | | |
|---|---|---|
| CN | 1647774 A | 8/2005 |
| CN | 1695565 A | 11/2005 |
| DE | 4038295 A1 | 6/1992 |
| DE | 102006060070 A1 | 2/2008 |
| DE | 102009042276 A1 | 4/2011 |
| DE | 102011109069 A1 | 1/2013 |
| EP | 0194856 A2 | 9/1986 |
| EP | 0329492 A2 | 8/1989 |
| EP | 1882454 A2 | 1/2008 |
| EP | 1513463 B1 | 5/2011 |
| JP | H02161937 A | 6/1990 |
| JP | 0576539 A | 3/1993 |
| JP | H0584253 A | 4/1993 |
| JP | 05228158 A | 9/1993 |
| JP | H05285159 A | 11/1993 |
| JP | H0686782 A | 3/1994 |
| JP | 06217986 A | 8/1994 |
| JP | 4982638 B2 | 7/2012 |
| WO | 9214415 A2 | 9/1992 |
| WO | 9406380 A1 | 3/1994 |
| WO | 2005037062 A2 | 4/2005 |
| WO | 2011133922 A2 | 10/2011 |
| WO | 2013145708 A1 | 10/2013 |
| WO | 2013154708 A1 | 10/2013 |

OTHER PUBLICATIONS

Medsolution—an operating division of Medical Tourism Inc., "Lithotripsy", 4 pages, 2008 http://www.medsolution.com/surgery_urogen-lithotripsy.asp.

Orkisz et al., "Image Based Renal Stone Tracking To Improve Efficacy In Extracorporeal Lithotripsy", The Journal of Urology, vol. 160, Issue 4, pp. 1237-1240, Oct. 1998.

Wolf, S., U.S. Appl. No. 14/269,150, filed May 4, 2014.

Finkman et al., U.S. Appl. No. 14/076,314, filed Nov. 11, 2013.

Waingankar et al., "Guidewires and Angled Catheters", Springer Science+Business Media New York, pp. 127-136, 2013.

International Application # PCT/US2015/026571 Search Report dated Jun. 16, 2015.

International Application # PCT/US2015/026572 Search Report dated Jun. 12, 2015.

International Application # PCT/US14/58147 Search Report dated Jan. 29, 2015.

U.S. Appl. No. 14/076,314 Office Action dated Jul. 8, 2015.

U.S. Appl. No. 14/076,314 Office Action dated Oct. 8, 2015.

* cited by examiner

COMPUTER AIDED IMAGE-BASED ENHANCED INTRACORPOREAL LITHOTRIPSY

BACKGROUND OF THE INVENTION

1. Field of the Invention

This invention relates to removal of calculi from the body. More particularly, this invention relates to intracorporeal comminution of urinary calculi.

2. Description of the Related Art

Nowadays, lithotripsy for urinary stones can be carried out by extracorporeal shockwave lithotripsy or endoscopically. The latter approach is known as intracorporeal lithotripsy. Intracorporeal lithotripsy may be conducted by flexible or rigid ureteroscopy or percutaneous nephrolithotomy. Intracorporeal lithotripsy is typically accomplished using laser energy. However, other technologies such as ballistic lithotripsy, ultrasonic lithotripsy and electrohydraulic lithotripsy are applied by instrumentation of the urinary tract.

Current instruments for intracorporeal lithotripsy have several disadvantages:

There is poor control of the outcome. By trial and error, the urologist must manually adjust the power settings, activate the instrument, and determine that the desired outcome for the case at hand has resulted. This process is usually iterated, thereby prolonging the procedure. In addition, the parameters available for change by the urologist are limited. Moreover, there is frequently no clear relation between the instrument settings and the effect on the calculus being treated.

Stone migration away from the endoscope, known as retropulsion, is a generally undesirable effect of lithotripsy. Retropulsion creates a need to further adjust or reposition the instrument, which prolongs the procedure and increases its cost. Moreover, in the case of ureteroscopy, migration of the stone up the ureter might result in its entering the renal pelvis, which could necessitate the use of another piece of equipment to complete the procedure, thereby increasing costs and possibly increasing morbidity.

Fragmentation of the stone is a desirable effect of lithotripsy. However, conventional techniques and instruments provide limited and inefficient control over the size of the stone fragments. Typically, fragments of various sizes break off from the main body of the stone. As a rule of thumb, stone fragments, which are bigger than 2 mm must be treated either by extraction or by further fragmentation. Smaller fragments are desirable, as they may be left in place. Currently, in the case of endoscopy, the urologist can only estimate the stone size by comparing the stone with the laser fiber, which has a known diameter in the image. Such estimates may be inaccurate.

There is a tradeoff between increasing power settings, which results in more fragmentation but with a greater degree of stone migration. Furthermore, increasing the power tends to produce larger fragments. Therefore, the urologist must make a compromise.

SUMMARY OF THE INVENTION

According to disclosed embodiments of the invention, methods and systems are provided for controlling the power parameters of an intracorporeal lithotripsy device in order to achieve a desired comminution of a calculus without the undesirable effects noted above.

There is provided according to embodiments of the invention a medical apparatus configured to deliver destructive energy to a stone. The apparatus includes a detector operative to obtain image data from the stone, a generator operating according to one or more producing parameters for producing the destructive energy, a video processor unit receiving the image data from the detector, wherein the video processor unit is operative to analyze the image data to determine a displacement of the stone relative to a previous location of the stone after the device has been actuated. The apparatus includes a controller linked to the video processor unit and to the generator, the controller being operative to vary the one or more producing parameters of the generator responsively to the displacement of the stone.

According to one aspect of the apparatus, the video processor unit is programmed to issue an alert when the displacement exceeds a displacement threshold.

According to a further aspect of the apparatus, the video processor unit is programmed to calculate a rate of movement of the stone, and to issue a motion alert when the rate of movement exceeds a velocity threshold.

According to still another aspect of the apparatus, the video processor unit is operative to determine that a change in a number of fragments of the stone has occurred.

According to an additional aspect of the apparatus, the device comprises an endoscope, and the destructive energy comprises a laser beam.

According to another aspect of the apparatus, the destructive energy comprises acoustic energy.

There is further provided according to embodiments of the invention a method, which is carried out by determining a first location of a stone within the body of a subject, directing destructive energy toward the stone, thereafter determining that a migration of the stone to a second location has occurred. The method is further carried out by establishing new parameters for the energy responsively to a difference between the second location and the first location, and iterating directing destructive energy using the new parameters.

According to one aspect of the method, directing destructive energy is performed using an endoscope, and the destructive energy is a laser beam.

According to yet another aspect of the method, directing destructive energy is delivered using an extracorporeal lithotripter, and the destructive energy is acoustic energy.

According to a further aspect of the method, determining a first location and determining that a migration of the stone has occurred includes optical imaging of the stone.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily always needed for practicing the present invention. In this instance, well-known circuits, control logic, and the details of computer program instructions for conventional algorithms and processes have not been shown in detail in order not to obscure the general concepts unnecessarily.

Figure 1:
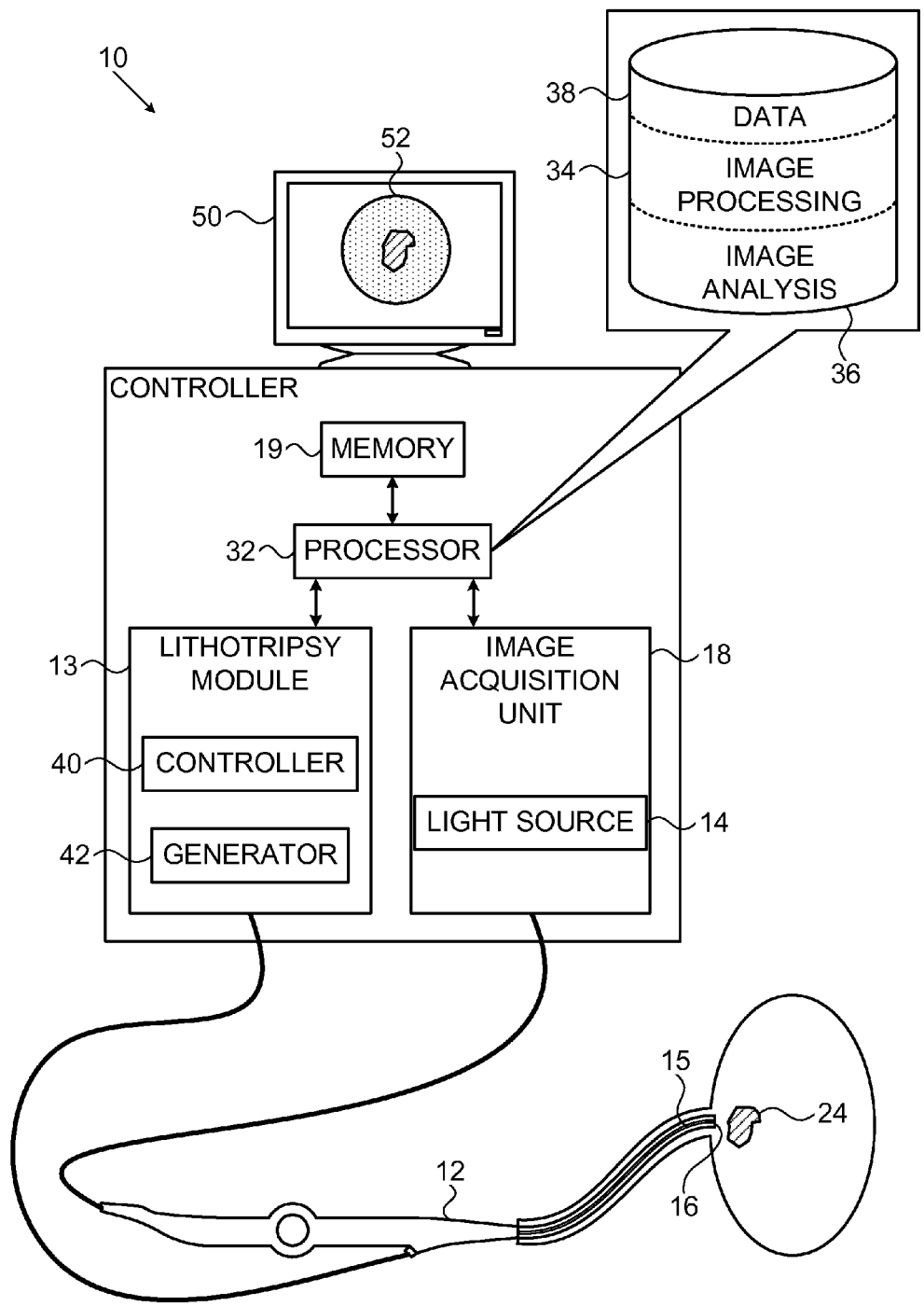
FIG. 1 is a pictorial schematic diagram of a system in accordance with an embodiment of the invention.

Turning now to the drawings, Reference is initially made to FIG. 1, which is a pictorial schematic diagram of a system 10, in accordance with an embodiment of the invention. A conventional endoscope 12 is adapted for intracorporeal lithotripsy. For example, the endoscope 12 can be a ureteroscope or a nephroscope for percutaneous entry to the renal pelvis. The endoscope 12 may be equipped for any form of intracorporeal lithotripsy known in the art, including laser lithotripsy, electrohydraulic lithotripsy, pneumatic lithotripsy, ultrasonic lithotripsy, and combinations thereof. Energy produced by a lithotripsy module 13 is projected through a working channel 15 of the endoscope 12, which may include an optical probe comprising fiberoptics and an optical lens (not shown) for transmitting light from a source 14 to calculus 24. The endoscope 12 may include a lens system and semi-conducting imaging array (described below) at distal end 16 for returning reflected light to an image acquisition unit 18. The source 14 may emit light at one or more wavelengths.

The image acquisition unit 18 can be realized as the device described in U.S. Pat. No. 8,659,646, which is herein incorporated by reference.

Figure 2:
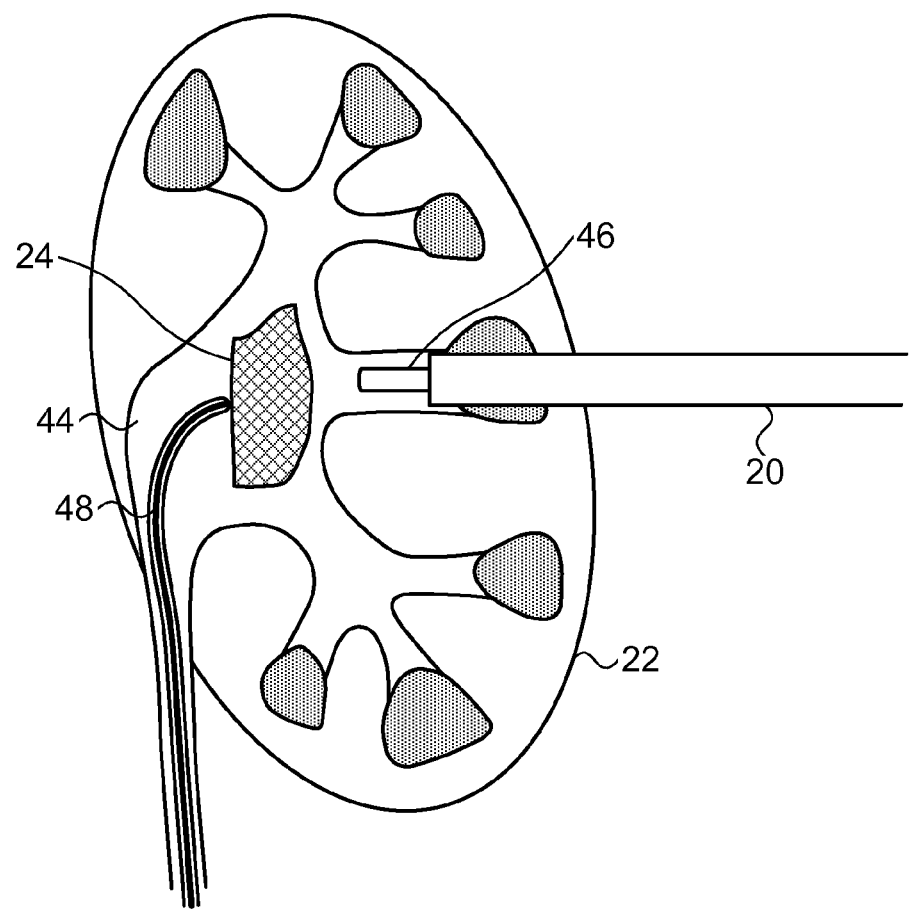
FIG. 2 is a composite drawing illustrating techniques of intracorporeal lithotripsy suitable for use with the system shown in FIG. 1, in accordance with alternate embodiments of the invention.

Reference is now made to FIG. 2, which is a composite schematic drawing illustrating techniques of intracorporeal lithotripsy suitable for use with the system 10 (FIG. 1), in accordance with embodiments of the invention. A nephroscope 20 as an endoscope for this procedure enters kidney 22 percutaneously to treat calculus 24 located in renal pelvis 44. The nephroscope 20 has a hollow channel (not shown) through which an optical fiber 46 can be inserted and placed in proximity with the calculus 24. Alternatively, a ureteroscope 48 can be passed in a retrograde direction through the urinary tract to approach the calculus 24. The nephroscope 20 and ureteroscope 48 can incorporate the various intracorporeal lithotripsy technologies noted above.

Reverting to FIG. 1, the image acquisition unit 18 provides image data to a processor 32. The processor 32 typically comprises a general purpose or embedded computer processor, which is provided with a memory 19, and programmed with suitable software for carrying out the functions described hereinbelow. Thus, although the processor 32 is shown as comprising a number of separate functional blocks, these blocks are not necessarily separate physical entities, but rather represent different computing tasks or data objects stored in a memory that is accessible to the processor. These tasks may be carried out in software running on a single processor, or on multiple processors. The software may be embodied on any of a variety of known non-transitory media for use with a computer system, such as a diskette, or hard drive, or CD-ROM. The code may be distributed on such media, or may be distributed to the processor 32 from the memory or storage of another computer system (not shown) over a network. Alternatively or additionally, the processor 32 may comprise a digital signal processor or hard-wired logic.

The processor 32 is programmed to execute image processing routines 34, and to determine characteristics of the calculus using analysis programs 36, as described in further detail below. A database 38 of time-varying characteristics of the current calculus accumulated from actuations of the generator may be stored and a statistical model prepared, taking into consideration the parameters described herein. Using these characteristics, the processor 32 calculates optimum power parameters, and transmits control signals to a controller 40 of lithotripsy module 13, which adjusts the power settings of a generator 42 responsively to one or more energy producing parameters. A monitor 50 may present an image 52 of the calculus being treated.

TABLE 1

| Parameters |
|---|
| Power |
| Pulse rate |
| Pulse width |
| Distance from tip |
| Retropulsion |
| Stone Size |
| Fragment Size |
| Stone Composition |

Table 1 is an exemplary table illustrating parameters that may affect power settings.

The first three parameters in Table 1 are controllable by the operator or the processor 32. In some embodiments, the processor 32 may robotically manipulate the endoscope 12 and affect the distance between the tip and the calculus. The last parameter, stone composition, may be known, estimated or entirely unknown, It is clearly not controllable, but may have a significant effect on fragment size. For example, a cysteine or uric acid stone can be expected to respond to a laser pulse differently from a calcium oxalate stone.

The generator 42 produces the destructive energy to be applied to the calculus 24, according to the above-noted types of intracorporeal lithotripsy being employed. Thus, the destructive energy may comprise a laser beam. In any case, the energy is transmitted by the lithotripsy module 13 and directed at a calculus that lies beyond the distal end 16. A series of images of the calculus are acquired by the image acquisition unit 18, which includes images taken before and after the energy application.

Figure 3:
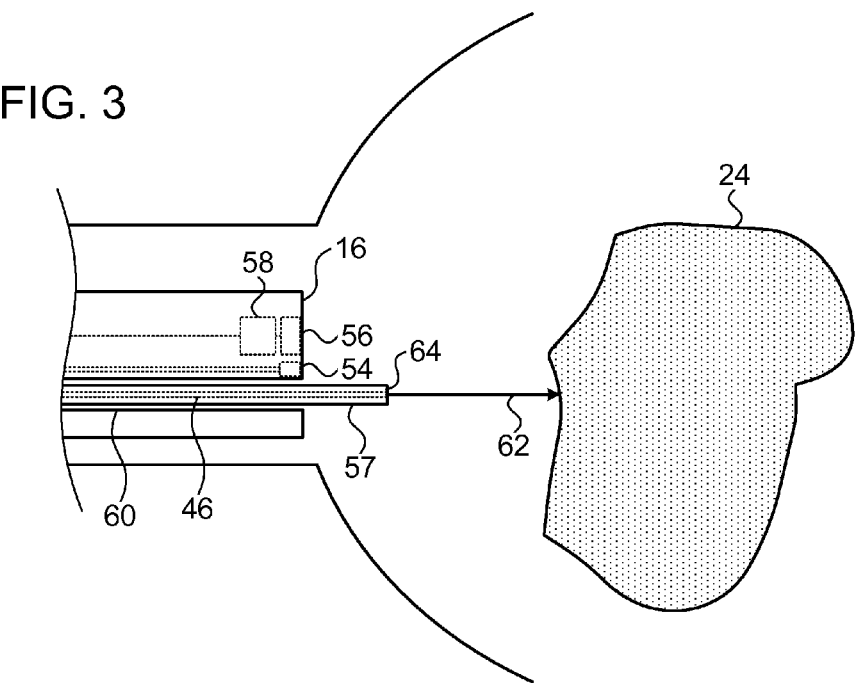
FIG. 3 is a schematic diagram illustrating the distal end of the endoscope shown in FIG. 1 in accordance with an embodiment of the invention.

Reference is now made to FIG. 3, which is a schematic diagram illustrating the distal end 16 of endoscope 12 (FIG. 1), in accordance with an embodiment of the invention. The distal end 16 is assumed to be in proximity to calculus 24. An illuminator 54 is able to radiate visible light, typically white light, under control of the image acquisition unit 18 (FIG. 1). Returning light from an object illuminated by illuminator 54 is focused by a lens system 56 onto a semiconducting imaging array 58, which is also controlled by the image acquisition unit 18, and which enables capture of an image of the illuminated object. In the example of FIG. 3, a probe 57 traverses working channel 60 and is configured to be able to transmit a laser beam produced by the generator 42 in the lithotripsy module 13 through the optical fiber 46 (FIG. 1) and along a path 62 extending from distal end 64. The laser beam conveys sufficient energy to break or fracture calculus 24.

Laser Operation.

The typical laser's power parameters are the repetition rate (number of laser pulses per second), the energy per pulse and the pulse width.

Figure 4:
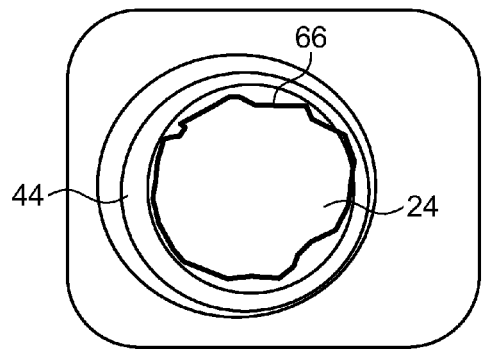
FIG. 4 is a diagram showing a calculus as viewed through an endoscope in accordance with an embodiment of the invention.
Figure 5:
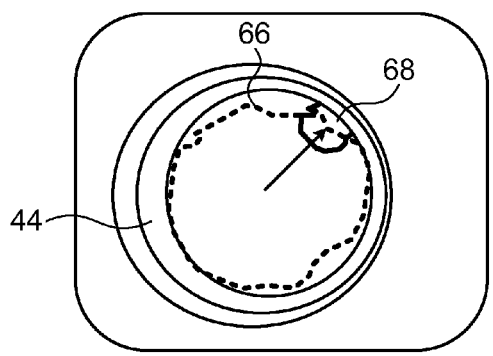
FIG. 5 is a diagram showing a calculus as viewed through an endoscope in accordance with an embodiment of the invention.

Reference is now made to FIG. 4 and FIG. 5, which are diagrams showing calculus 24 in renal pelvis 44 as viewed as an image acquired by semiconductor imaging array 58 (FIG. 3) at the distal end of an endoscope in accordance with an embodiment of the invention. The calculus 24 is seen before lithotriptic energy application, and during or after lithotriptic energy application in FIG. 4 and FIG. 5, respectively, and its contour line 66 indicated. In FIG. 5 the calculus 24 has been moved deeper into the renal pelvis 44. Its original contour line 66 is shown as a broken line. A fragment 68 remains and has been displaced beyond the contour line 66. During the firing of the laser on the stone, the system detects and tracks the stone in the image, and continuously measures the stone's motion, e.g., retrograde motion and fragmentation using the analysis programs 36 (FIG. 1). In the example of FIG. 5i an arrow indicates movement of the calculus 24. Such movement may occur when the power applied to the calculus 24 is excessive. In a subsequent energy application, the power should be lowered to increase the likelihood that the calculus will fragment without retrograde motion. It is known that lower energy per pulse and longer pulse width result in less stone retropulsion. It is also known that lower energy per pulse and longer pulse width results in smaller fragments and vice versa. Size measurements of the stone and fragments can be based on the known size of the laser fiber, the spot of the aiming beam e.g., through the fiberoptics of the lithotripsy device or the safety guide wire e.g., projected through the working channel.

During laser lithotripsy, the fiber tip is typically placed in contact with the stone's surface or in close proximity to the stone, typically within 1 mm. By calculating the relation between the size of the tip in the image with the size of the stone fragment in the image, based on the absolute size of the tip, the size of the fragment 68 can be calculated.

Calculation of stone size may also be based on detection of the laser aiming beam. During laser lithotripsy an aiming beam, having a red or green color, is transmitted through the fiber along the path 62 together with an ablating laser beam, which is invisible to the human eye. The visible beam indicates the location of the target. The beam diameter seen on the surface of the stone is determined by the known size of the fiber used. The stone and fragment sizes may be calculated with reference to the beam diameter. Fiber diameters of 200, 270 or 365 μm are suitable. These values are not critical.

Figure 6:
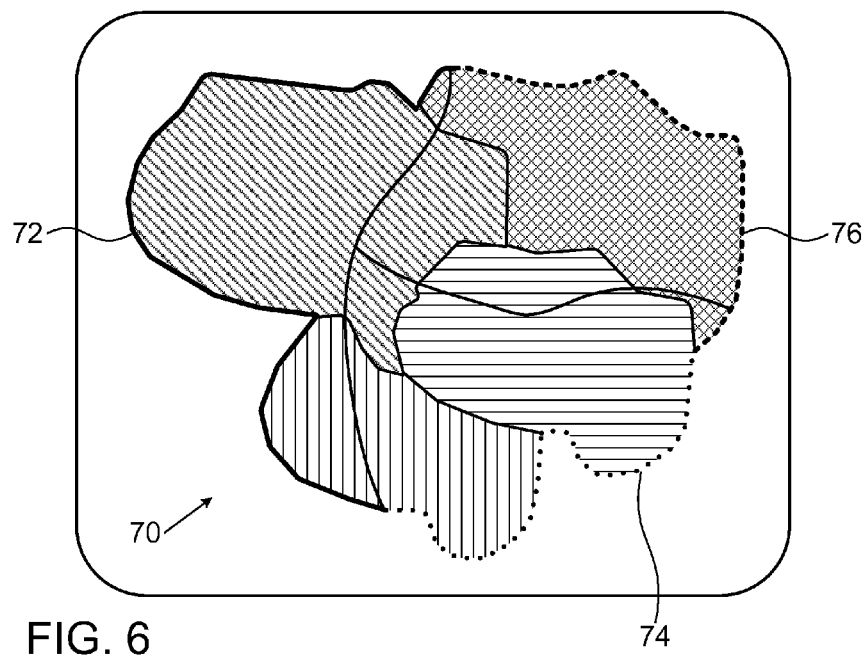
FIG. 6 is a schematic diagram of an optical image of a calculus in accordance with an embodiment of the invention.

Reference is now made to FIG. 6, which is a schematic diagram of an optical image of a calculus 70 typically presented to an operator on monitor 50 (FIG. 1) in accordance with an embodiment of the invention. It will be seen from the discussion below that application of destructive energy by intracorporeal lithotripsy as described above causes the calculus 70 to disintegrate into fragments.

Figure 7:
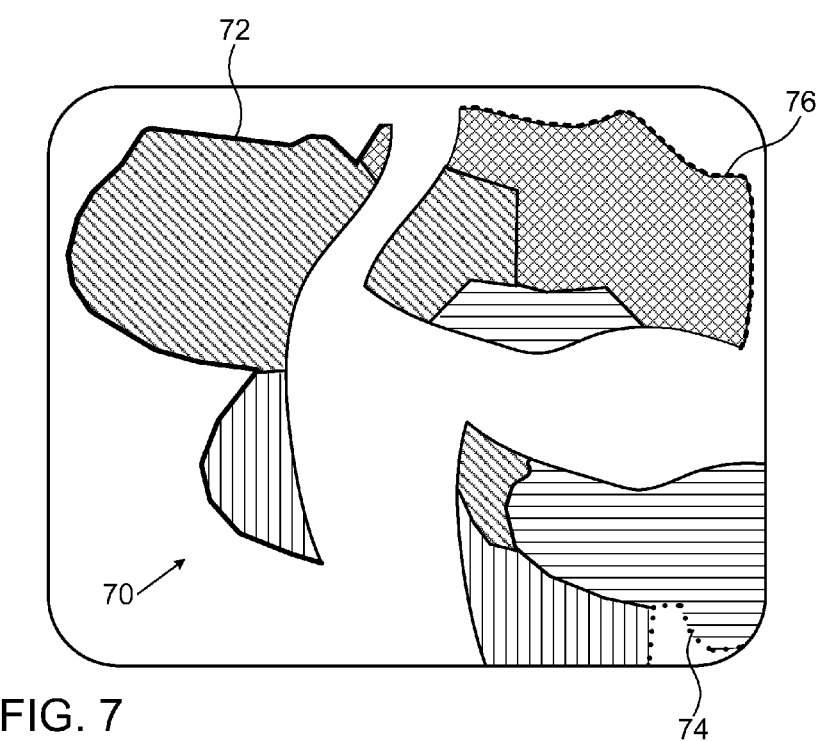
FIG. 7 is a schematic diagram of an optical image of the calculus shown in FIG. 6 taken after a lithotriptic energy application, in accordance with an embodiment of the invention.

Reference is now made to FIG. 7, which is a schematic diagram of an optical image of calculus 70 taken after an energy application, in accordance with an embodiment of the invention. Disruption of the calculus 70 into fragments is evident. The exterior surfaces of the fragments are delineated by contour lines 72, 74, 76. Contour lines 72, 74, 76 were generated by the processor, and used to track the movements of the fragments. Tracking may be performed well-known methods of image analysis. One suitable technique is disclosed in U.S. Pat. No. 5,697,885, which is herein incorporated by reference.

The image is only partially seen. Although prior to treatment, the calculus 70 was entirely visualized, now fragment 74 has been displaced and is not entirely within the field of view. While the fragments shown in FIG. 7 are shown as relatively large with respect to the original mass of the calculus 70 in FIG. 6 for clarity of presentation, this is not always the case. Indeed, the fragments are typically much smaller than presented in this example.

Figure 8:
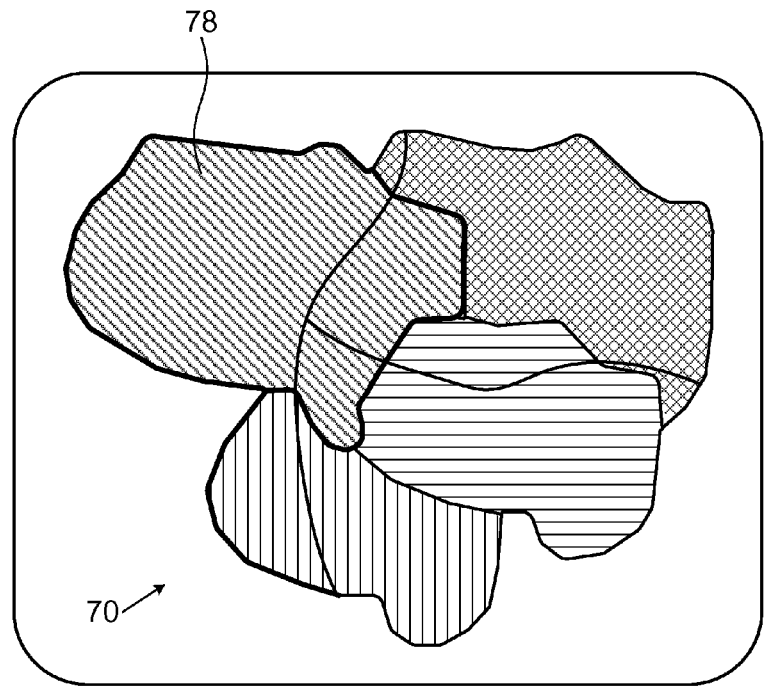
FIG. 8 is a detailed pretreatment schematic diagram of a calculus in accordance with an embodiment of the invention.
Figure 9:
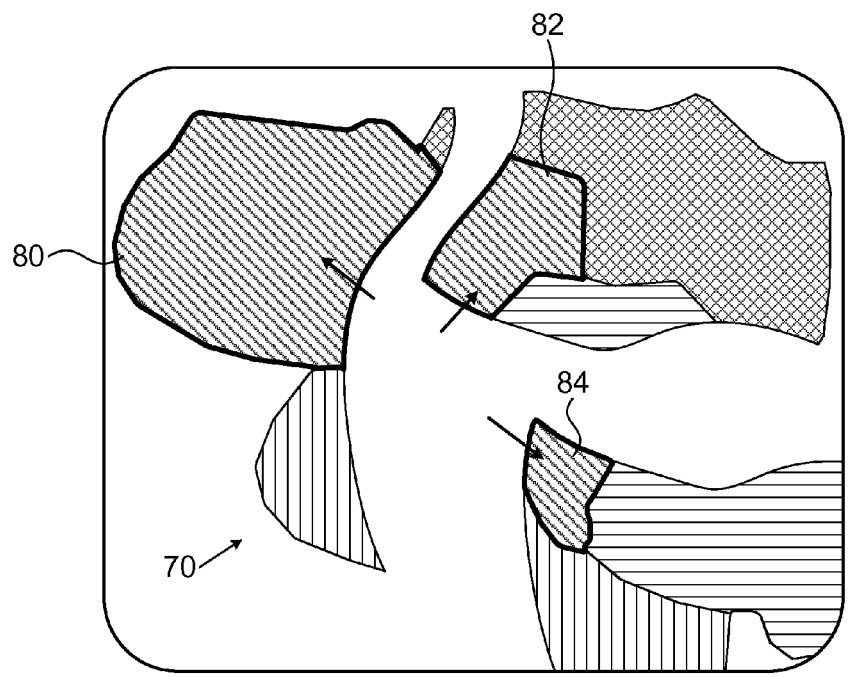
FIG. 9 is a detailed posttreatment schematic diagram of a calculus in accordance with an embodiment of the invention.

Stone fragments movement also can be tracked using algorithms known in the art for the detection of a stone's contour line, e.g., contour line 66 (FIG. 4) and detecting a change in location of the contours in successive frames. Reference is now made to FIG. 8 and FIG. 9, which are detailed pretreatment and posttreatment schematic diagrams of a calculus 70 similar to FIG. 6 and FIG. 7. These figures illustrate the use of color for motion tracking of the calculus 70. Hatching patterns in different regions of the calculus 70 delineate regions of different fragments on images of the calculus. One method of motion tracking exploits differences in the stone's and/or fragments color from its surroundings. For example, region 78 in FIG. 8 is no longer intact in the fragmented calculus of FIG. 9. Rather, portions of region 78 appear as smaller regions 80, 82, 84 in separate fragments. Detecting color contrast alone or in combination with edge detection algorithms provides sufficient information to determine a change in location of the stone in different frames.

In one mode of operation, The system gradually increases the power parameters, the pulse width or both according to a predefined algorithm while continuously tracking actual performance. For example, one order of changing the power parameters is a 10% increase in energy followed by a 10% increase in pulse width in two successive firings. Additionally or alternatively, the operator may vary the distance between the endoscope and the calculus, recognizing that with laser techniques, efficiency drops off rapidly when a distance of about 1 mm is exceeded. Once the system detects a certain amount of retropulsion, it reacts by stabilizing or reducing the power parameters.

Power parameters in successive frames may be set automatically, with or without confirmation by the operator, and optionally with reference to the model described above to verify that the stone is responding according to the model's predictions.

Non-Laser Intracorporeal Lithotripsy.

The technique described above can be applied mutatis mutandis, to the other types of intracorporeal lithotripsy noted above, like a basket lithotripsy device or an ultrasonic probe. For example, while stone and fragment size cannot be determined using the laser's aiming beam, they can be estimated using the known size of the lithotripter probe or image processing by image recognition program. By the detection of stone fragments, the lithotripsy module can vary the destructive energy applied to the stone. Varying the distance from the endoscope to the calculus may be more influential in ballistic techniques than with lasers and can be controlled to some extent by the operator.

Operation.

Figure 10:
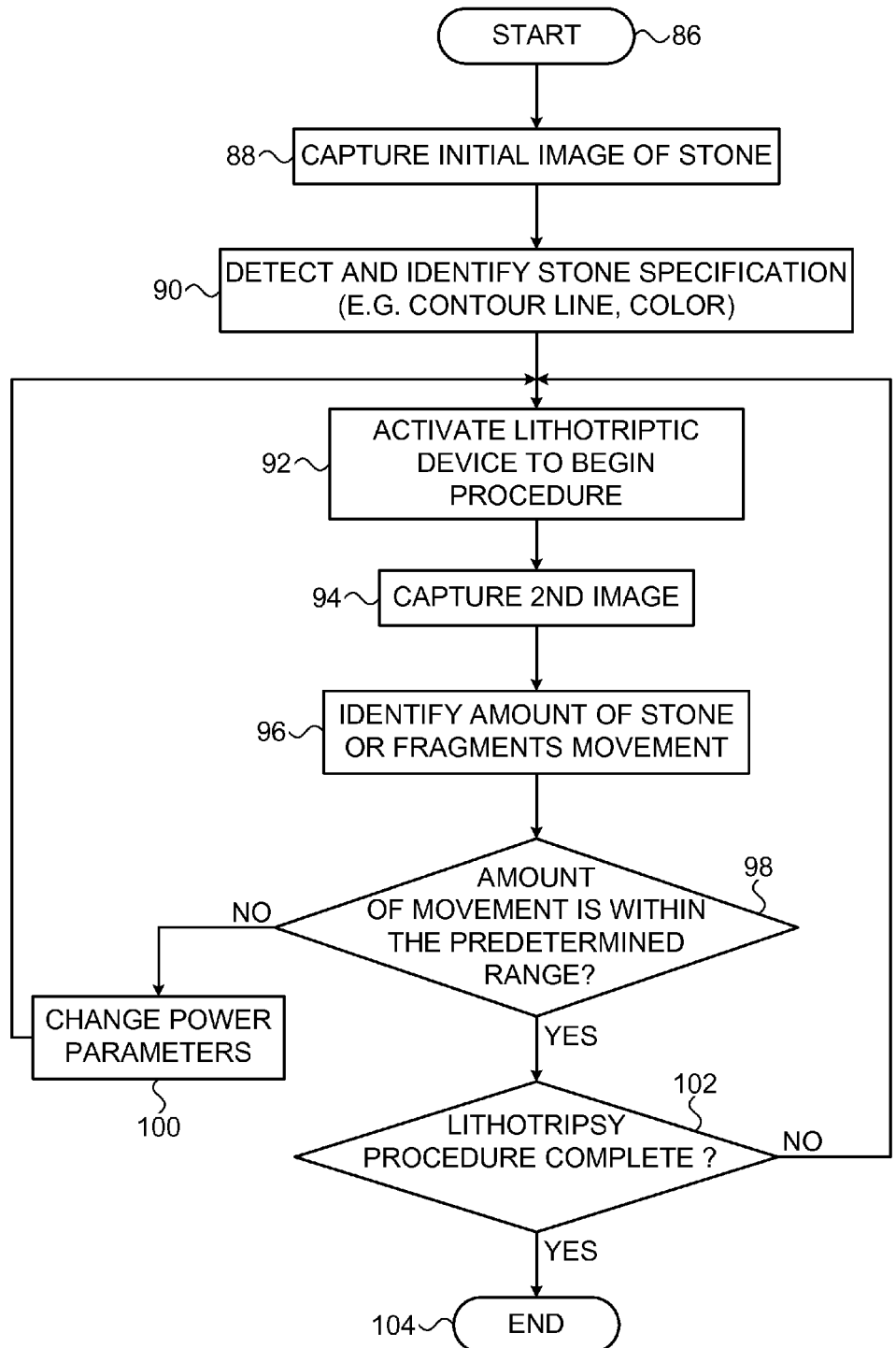
FIG. 10 is a flow chart of a method of intracorporeal lithotripsy, in accordance with an embodiment of the invention.

Reference is now made to FIG. 10, which is a flow-chart of a method of intracorporeal lithotripsy, in accordance with an embodiment of the invention. The procedure begins at initial step 86. A subject is intubated with an endoscope, typically a ureteroscope or a nephroscope as described above and placed into contact with or proximity with a calculus. The endoscope is provided with optical imaging capabilities and an energy delivery system as noted above. Next, at step 88 an initial optical image of the calculus is acquired.

Next, at step 90 the image is analyzed to establish its contour lines and/or color regions of the calculus. Power parameters of an intracorporeal lithotriptic device are set to initial values, which may vary according to the information obtained from the initial optical image.

Next, at step 92 the lithotriptic device is activated. Destructive energy is transmitted through the endoscope and applied to the calculus.

Next, at step 94, after completion of step 92, a second optical image of the calculus is acquired.

Next, at step 96 the second optical image is analyzed to establish the size of the calculus remaining, the number of fragments, and the movement of the calculus and fragment from the position prior to performance of step 92.

Next, at decision step 98, it is determined if the amount of movement of the calculus and its fragments is within a predetermined range, e.g., 1 mm. If the determination is negative, then control proceeds to step 100. The power parameters of the lithotriptic device are adjusted. Control then returns to step 92 to iterate the activation of the lithotriptic device, using the new power parameters.

If the determination at decision step 98 is affirmative, then control proceeds to decision step 102, where it is determined if the lithotripsy procedure is complete. If the determination is negative, then control returns to step 92 to iterate the activation of the lithotriptic device.

If the determination at decision step 98 is affirmative, then control proceeds to final step 104 and the procedure ends.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A medical apparatus for preforming lithotripsy, comprising:
   a device configured to deliver a destructive energy to a stone;
   a detector operative to obtain image data from the stone;
   a generator including one or more producing parameters for producing the destructive energy;
   a video processor unit, which is coupled to receive the image data from the detector and is operative to analyze the image data under control of software to establish a contour line of the stone and thereby to determine a displacement of the stone relative to a previous location of the stone responsively to an actuation of the device to deliver the destructive energy, and is programmed to issue an alert when the displacement exceeds a displacement threshold; and
   a controller linked to the video processor unit and to the generator, the controller operative to vary the one or more producing parameters of the generator in response to control signals from the video processor unit responsively to the displacement of the stone.

2. The apparatus according to claim 1, wherein the video processor unit is programmed to calculate a rate of movement of the stone, and to issue a motion alert when the rate of movement exceeds a velocity threshold.

3. The apparatus according to claim 1, wherein the video processor unit is operative to determine that a change in a number of fragments of the stone has occurred.

4. The apparatus according to claim 1, wherein the device that is configured to deliver the destructive energy comprises an endoscope, and the destructive energy comprises a laser beam.

5. The apparatus according to claim 1, wherein the destructive energy comprises acoustic energy.

* * * * *